United States Patent [19]

Chikama

[11] 4,336,794
[45] Jun. 29, 1982

[54] GUIDE TUBE

[75] Inventor: Toshio Chikama, Tokyo, Japan

[73] Assignee: Machida Endoscope Co., Ltd., Tokyo, Japan

[21] Appl. No.: 198,351

[22] Filed: Oct. 20, 1980

Related U.S. Application Data

[63] Continuation of Ser. No. 968,024, Dec. 11, 1978, abandoned.

[30] Foreign Application Priority Data

Feb. 1, 1978 [JP] Japan ............................ 53-10087[U]

[51] Int. Cl.³ .............................................. A61B 1/00
[52] U.S. Cl. ........................................ 128/4; 128/348
[58] Field of Search ............... 128/350 R, 348, 349 R, 128/351, 3–8; 138/DIG 3, DIG. 9, 137, 145, 149; 427/2, 385 B; 428/36, 422

[56] References Cited

U.S. PATENT DOCUMENTS 2,112,737  3/1938  Dodge ............................ 128/350 R
3,094,762  6/1963  Jackel ............................ 128/348 A
3,106,483 10/1963  Kline et al. .................... 128/348 X Primary Examiner—John D. Yasko
Attorney, Agent, or Firm—Berger & Palmer

[57] ABSTRACT

The present invention discloses herewith guide tube with favorable flexibility and water-tightness. A watertight coating is provided on at least one side of the inner and exterior surface of a porous tube which bends continuously keeping its tubular shape. By these provisions, a guide tube is obtained which is easily inserted with an endoscope into a body cavity or is smoothly inserted into bronchia as an anesthetic tube.

4 Claims, 4 Drawing Figures

GUIDE TUBE

This is a continuation of application Ser. No. 968,024, filed Dec. 11, 1978, now abandoned.

BACKGROUND OF THE INVENTION

A. Field of the Invention

The present invention generally relates to a guide tube with favorable flexibility and water-tightness, or more particularly, to a guide tube which is easily inserted with an endoscope into a body cavity or is smoothly inserted into bronchia as an anesthetic tube.

B. Description of the Prior Art

An endoscope is an optical instrument which utilizes flexible optical bundles for observing means in order to transmit an image of an object caught at a forward portion to an eyepiece of a grip and is used for inspecting or treating a cancer or a polyp in a body cavity. The forward portion with angle deflective means and a flexible sheath composed of spiral wires are inserted into the body cavity for inspection. But, direct insertion of these elements frequently results in bleeding or a difficulty in insertion, because the inner side of the body cavity is complicated.

For this reason, a guide tube is attached round the forward portion and the flexible sheath when inserting them into the body cavity in order to prevent an injury or to have a smooth insertion. In addition, the endoscope can be inserted several times by way of the guide tube, if it is left in the body cavity.

In an anesthetic operation, an anesthetic drug is forwarded into the lungs by way of an anesthetic tube which is inserted into the bronchia.

Accordingly the, above-said guide tube or the anesthetic tube must be in the first place smooth between the body cavity and also be good in water-tightness for shutting off a body fluid, cleanser, or the anesthetic drug. Further, the guide tube must bend itself continuously keeping its tubular shape.

Formerly, a synthetic resin tube was used for the guide tube which is indeed good in its water-tightness, but the tubular form is constricted at the minimum point of the radius of curvature as shown in FIG. 1, when it is inserted in the complicated body cavity. Further, insertion in a body cavity is difficult when the tube is too thick in order to cope with above-said defect.

While a vinyl chloride tube is formerly used for an anesthetic tube, its flexibility is not so good and high-temperature sterilization is not possible due to the fact that it begins to soften at 80 degrees.

SUMMARY OF THE INVENTION

The present invention aims at providing a guide tube with favorable flexibility and water-tightness.

A water-tight coating is provided on at least one side of the inner and exterior surface of a porous tube which bends continuously keeping its tubular shape.

It is the first object of the invention to provide a guide tube which can easily be inserted into a body cavity with an endoscope.

It is the second object of the invention to provide a guide tube which can smoothly be inserted into the bronchia as an anesthetic tube.

The above and further objects and novel features of the invention will more fully appear from the following detailed description when the same is read in connection with the accompanying drawings. It is to be expressly understood, however, that the drawings are for purpose of illustration only and is not intended as a definition of the invention.

DETAILED DESCRIPTION OF PREFERRED EMBODIMENTS

The construction of the present invention is now described herein-under with reference to the figures.

Figure 1:
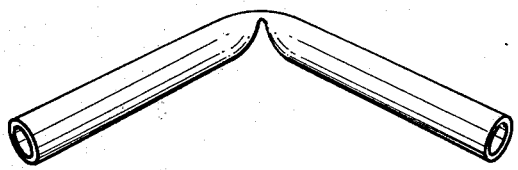
FIG. 1 is a schematic illustration showing a prior art guide tube which is constricted at the minimum point of the radius of curvature.
Figure 2:
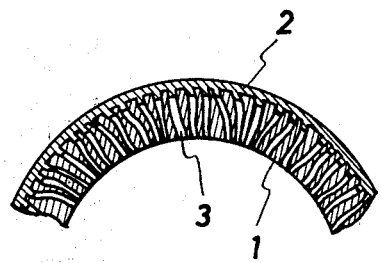
FIG. 2 is an enlarged cross-sectional view of an embodiment according to the present invention.

In FIG. 2, a water-tight coating 2 is provided on at least one side of the inner and exterior surface of a porous tube 1 which bends continuously keeping its tubular shape.

A polytetrafluoroethylene tube with microns of fine holes 3 in the radial direction may be used for the porous tube 1.

The water-tight coating 2 may be formed by coating a fluorocarbon elastomer on the porous tube 1. Besides, a slight coating of the water-tight coating 2 on the holes 3 serves the purpose. An excess amount of water-tight coating 2 results in the lack of flexibility.

Figure 3:
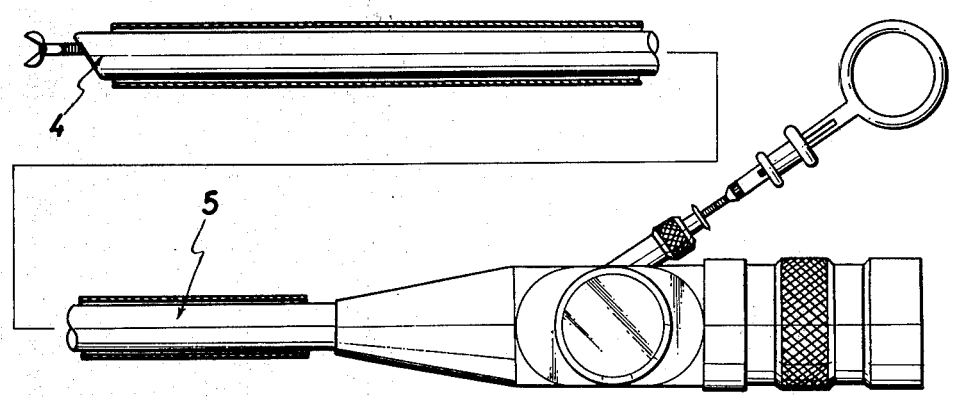
FIG. 3 is a schematic illustration of an endoscope to which is attached the guide tube according to the invention.
Figure 4:
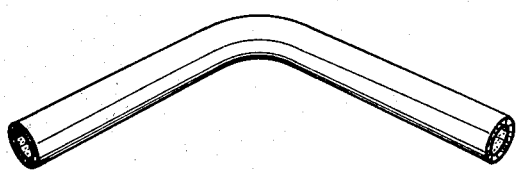
FIG. 4 is a schematic illustration of the guide tube according to the invention which is bent.

In the next place, an operation and an effect of the invention is described when the guide tube is used with an endoscope. Said guide tube is attached to the forward portion 4 and the flexible sheath 5, as shown in FIG. 3, when inserting the endoscope into the body cavity. The water-tight coating 2 serves as a smooth insertion surface of the guide tube into a body cavity. Said porous tube 1 also serves as the smooth insertion as the tube keeps its tubular form even if it is inserted into a complicated body cavity. On the top of it, the flexible sheath 5 can be inserted several times into the guide tube which is left in the body cavity because the tube bends continuously keeping its tubular form as shown in FIG. 4. The guide tube can be subjected to high-temperature so that sterilization is possible after using it.

Same as it is for a case that the guide tube is used for an anesthetic tube, it is smoothly inserted into bronchia as the tube has favorable flexibility and high-temperature sterilization is also possible. Further, the tube can be inserted into the bronchia by the guidance of the endoscope.

While there have been shown and described and pointed out the fundamental novel features of the invention as applied to preferred embodiments. It will be understood, however, that the various omissions and substitutions and changes in the form and details of the mechanism illustrated and its operation may be made by those skilled in the art without departing from the spirit of the invention.

What is claimed is:

1. A hollow elongated guide tube having open ends and a generally circular cross-section for insertion into the body through a body tube or cavity enabling a medical instrument to pass through said open ends to extend into the body, said guide tube comprising:

a porous material having exposed outer and interior surfaces, said interior surface of said porous material forming a substantially fixed circular cross-section, said circular cross-section having a diameter of a size to allow a medical instrument to pass therethrough, a water-proof coating placed on at least the exposed outer surface to form a water-proof outer surface for said guide tube, said guide tube being bendable to accommodate its insertion in the body, said porous material being compressible, said guided tube being bent and said porous material compressing at the bend maintaining said circular cross-section of said internal surface of said guide tube.

2. A guide tube as claimed in claim 1, wherein said porous material comprises polytetrafluoroethylene.

3. A guide tube as claimed in claim 1, wherein said water-proof coating comprises a fluorocarbon elastomer.

4. A guide tube as claimed in claim 3, wherein said fluorocarbon elastomer is coated onto said porous material.

* * * * *